United States Patent
Bhakuni et al.

(10) Patent No.: US 6,750,356 B1
(45) Date of Patent: Jun. 15, 2004

(54) SINGLE POT CONVERSION OF ARTEMISININ INTO ARTEETHER

(75) Inventors: Rajendra Singh Bhakuni, Lucknow (IN); Amit Tewari, Lucknow (IN); Tarun Singh, Lucknow (IN); Suman P. S. Khanuja, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/308,651

(22) Filed: Dec. 2, 2002

(51) Int. Cl.$^7$ .................. C07D 321/10; C07D 313/00

(52) U.S. Cl. .................. 549/348; 549/348; 549/354

(58) Field of Search .................. 549/348, 354

(56) References Cited

U.S. PATENT DOCUMENTS 5,011,951 A * 4/1991 Buchs et al. ............... 549/348
6,346,631 B1 * 2/2002 Jain et al. .................. 549/348

* cited by examiner

*Primary Examiner*—D. Margaret Seaman
*Assistant Examiner*—Raymond Covington
(74) *Attorney, Agent, or Firm*—TraskBritt

(57) ABSTRACT

The present invention provides a method for the preparation of arteether from artemisinin in one pot in just about 4 hours comprising reduction of artemisinin into dihydroartemisinin by less quantity of sodium borohydride in ethanol at room temperature in the presence of a novel polyhydroxy catalyst, acylation of dihydroartemisinin in the presence of an acid catalyst, extraction of arteether from an aqueous reaction mixture using 1% ethyl acetate in n-hexane followed by workup and purification of the impure arteether to yield 80–86% (w/w) pure alpha, beta arteether.

22 Claims, 1 Drawing Sheet

ARTEMISININ

REDUCTION
ACYLATION

ARTEETHER

Figure 1: Scheme
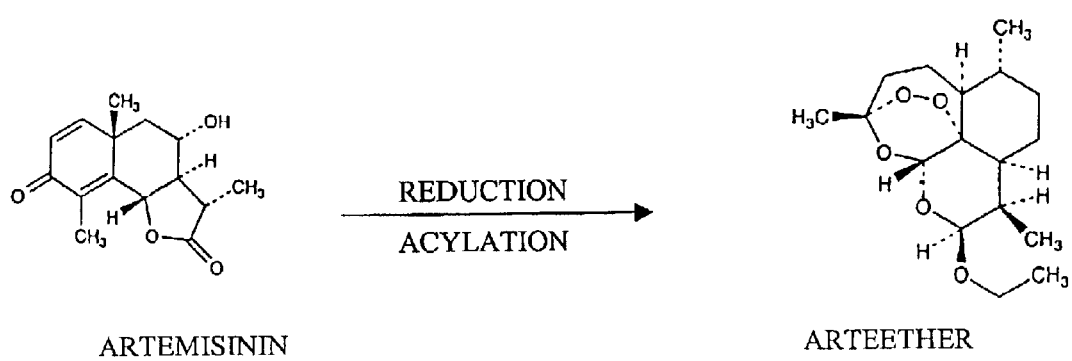
ARTEMISININ     REDUCTION / ACYLATION     ARTEETHER

SINGLE POT CONVERSION OF ARTEMISININ INTO ARTEETHER

FIELD OF INVENTION

The present invention relates to an improved single pot method for preparation of Arteether from Artemisinin. Arteether prepared from the process is useful for the treatment of uncomplicated, severe complicated and multi drug resistant malaria.

BACKGROUND OF THE INVENTION

Approximately, out of the 4 billion people suffering from malaria, 1–3 million people, mostly children die every year worldwide. The rapidly spreading multidrug resistant parasite to standard quinoline based antimalarial drugs such as chloroquine and mefloquine based antimalarial complicate chemotherapy treatment of malaria patients.

Artemisinin and its derivative artemether, arteether, artelinate and artesunate are a class of antimalarials compounds derived from *Artemisia annua* which are now proving their promising activity and are being used for the treatment of uncomplicated severe complicated/cerebral and multi drug resistant malaria. Dihydroartemisinin is derived from artemisinin, a sesquiterpene endoperoxide isolated from the plant *Artemisia annua*.

Arteether, a ethyl ether derivative of dihydroartemisinin, a drug introduced in India for the first time by Central Institute of Medicinal and Aromatic Plants (CIMAP), Lucknow, has undergone extensive preclinical, animal, toxicological studies as well as clinical studies on Indian subjects for drug regulatory purposes. World Health Organization (WHO) has also recommended arteether as life saving antimalarial drug. Arteether is more potential as compared to artemisinin and is an ideal antimalarial drug especially for treating multi drug resistant and complicated strains of *Plasmodium falciparum*. Arteether shows rapid schizoticial action with quicker clearance rate, short fever clearance time with no side effects and low recrudescence rate.

Brossi, et al (Brossi, A; Venugopalan, B; Domingueg, G L; Yeh, H. J. C; Flippend-Anderson, .J. L.; Buchs, P; Luo, X. D.; Milhous, W and peters, W; J. Med. Chem. 31, 646–649,1988) reported the preparation of arteether, the ethyl ether derivative of dihydroartemisinin in two steps: First artemisinin was reduced with an excess of sodium borohydride in methanol at 0 to −5° C. in 3 hours to dihydroartemisinin in 79% yield. In the second step, arteether is prepared by dissolving the dihydroartemisinin in the solvent mixture of benzene and ethanol at 45° C. followed by addition of $BF_3$ etherate and refluxing the reaction mixture at 70° C. for one hour. After the completion of the reaction it was worked up, dried over anhydrous sodium sulphate with removal of the solvent dichloromethane. The reaction yielded arteether along with some impurities. Column chromatography of the reaction mixture over silica gel, 1:20 ratio yielded pure alpha and beta arteether in nearly equal qualitative yield.

E L-Feraly et al. (E L Feraly, F. S; Al-Yahya M A; Orabi, K. Y; Mc-Phail D R and Mc Phail A. T. J. Nat. Prod. 55, 878–883, 1992) reported the preparation of arteether by a process in which anhydrodihydroartemisinin, prepared from artemisinin was dissolved in absolute alcohol. The reaction mixture was stirred in the presence of p-toluene sulphonic acid used as a catalyst. On workup it yielded a mixture of beta arteether and C-11 epimer in the ratio of 3:1. In this process only beta arteether is obtained and separation of C-11 epimer is difficult and preparation of anhydrodihydroartemisinin is a tedious process. The reaction took 22 hours to complete. The lewis acid catalyst used in this reaction is required in large amount (60 mg. acid catalyst by 100 mg. anhydrodihydroartemisinin.

In another method Bhakuni etal (Bhakuni, R. S.; Jain D. C and Sharma R. P. Indian. J. Chemistry, 34B, 529–30,1995) arteether, artemether and other ether derivatives were prepared from dihydroartemisinin in different alcohol and benzene in the presence of chlorotrimethylsilane catalyst in 2–4 hours at room temperature. After workup of the reaction mixture and removal of the solvent, the impure reaction products were purified over silica gel column to obtained the pure mixture of alpha, beta ethers.

Another method is reported by Lin et al. (Lin, A. J. and Miller, R. E, J. Med Chem. 38,764–770,1995). In this method the new ether derivatives were prepared by dissolving dihydroartemisinin in anhydrous ether and appropriate alcohol followed by $BF_3$-etherate. The reaction mixture was stirred at room temperature for 24 hours. The yield of the purified products ranged from 40–90%. Purification was achieved by the use of silica gel chromatography.

Yet another method described by Jain et al (Jain D. C, Bhakuni R. S, Saxena S, kumar, S and Vishwakarma, R. A. ref: U.S. Pat. No. 6,346,631, G.B. Application no 0007261.1 and German application no 10014669.4] teaches preparation of arteether from artemisinin which comprises: Reduction of artemisinin into dihydroartemisinin, isolation of dihydroartemisinin, conversion of dihydroartemisinin by dissolving it in alcohol and adding trialkylorthoformate in the reaction mixture, which produce ethers in quantitative yield in 10 hours at 40 degree C.

The above mentioned methods are not cost effective and are time consuming. Moreover, benzene, a carcinogenic solvent, used in the previous methods is not acceptable according to the health standard. Further, all the above methods require at least two separate steps to convert artemisinin into ethers i.e reduction of artemisinin into dihydroartemisinin in the first pot followed by isolation of dihydroartemisinin and then comes the second step of conversion of dihydroartemisinin into different ethers in the second pot.

The Assignees co-pending U.S. application Ser. No. 10/105,964 filed on Mar. 25, 2002 which is incorporated herein as prior art reference teaches a process for preparing artemether from artemisinin. It should be noted that the aforesaid application does not use a polyhydroxy compound as catalyst during the process of reduction of artemisinin into dihydroartemisinin. In the present application, the applicants have utilized a polyhydroxy compound as a catalyst during the step of reduction of artemisinin to dihydroartemisinin. The Applicants have been successful in reducing artemisinin to dihydroartemisinin at room temperature in the presence of the polyhydroxy compound. It should be noted that to carry out a reaction not only the reactants play an inportant role but also other reaction conditions like solvent used, cooling or heating, inert atmosphere etc. are also important. Such reaction conditions provide a particular structure steriochemistry to the reactant molecules leading to the desired product. Introduction of the polyhydroxy compound for the reduction of artemisinin into dihydroartemisinin provides the ideal environment to the reactant molecules (artemisinin or the reducing agent or both) to reeact at room temperature (20–30° C.) which other react only at temperature in the range of 0–5° C. Also, the Applicants have found that the extraction of arteether from an aqueous reaction mixture using 1% ethyl acetate in n-hexane avoids extraction of unwanted polar impurities as compared to use of dihydromethane in the co-pending application. Further, the Applicants have found that resin could not perform esterification and hence, only unrecoverable catalysts such as chlorotrimethylsilane and p-toluene sulphonic acid are used in the present process. Thus the process of the present invention can not be considered as being obvious to a person of ordinary skill in the art and present invention provides an efficient method for conversion of artemisinin to arteether.

OBJECT OF INVENTION

The object of the present invention is the development of cost effective and improved single step method for the preparation of arteether which possesses reduction of artemisinin into dihydroartemisinin in the presence of a catalyst, conversion of dihydroartemisinin into arteether followed by extraction of the same in a single pot.

SUMMARY OF THE INVENTION

The present invention provides a method for the preparation of arteether from artemisinin in one pot in just about 4 hours. The process of the present invention comprises: reduction of artemisinin into dihydroartemisinin by less quantity of sodium borohydride in ethanol at room temperature in the presence of a novel polyhydroxy catalyst, acylation of dihydroartemisinin in the presence of an acid catalyst followed by extraction of arteether from an aqueous reaction mixture using 1% ethyl acetate in n-hexane. Workup of the impure arteether followed by silica gel column chromatography in 1:5–10 ratio, yields 80–86% (w/w) pure alpha, beta arteether.

DETAILED DESCRIPTION OF THE INVENTION

Accordingly, the present invention provides a single step process for the preparation of arteether from artemisinin in one pot comprising the steps of:

a. dissolving artemisinin and a polyhydroxy catalyst in ethanol at room temperature to obtain a solution,
b. adding a reducing agent to step (a) solution, stirring the reaction mixture at a room temperature (20 to 30° C.) for about 0.5 to 2 hours to reduce artemisinin into dihydroartemisinin,
c. adding an acid catalyst to the reaction mixture of step (b) with cooling,
d. stirring the reaction mixture of step (c) for about 1 to 2 hours at room temperature,
e. adding cold water to the reaction mixture of step (d), extracting with a mixture of ethyl acetate and n-hexane, separating the organic layer,
f. washing the organic layer of step (e) with 0.5% aqueous sodium bicarbonate solution followed by water,
g. drying the washed organic layer of step (f) over anhydrous sodium sulphate, filtering, evaporating the organic layer to obtain a residue, and
h. purifying the residue thus obtained by silica gel column chromatography to obtain arteether.

In an embodiment of the present invention, the two reactions, namely reduction of artemisinin to dihydroartemisinin and alkylation of dihydroartemisinin into arteether are carried out in a single pot thereby avoiding the process of isolation of the intermediate dihydroartemisinin.

In another embodiment of the present invention, the time required for conversion of artemisinin into arteether is about 4 hours.

In yet another embodiment of the present invention, ethanol used acts as a solvent and an alkylating agent.

In still another embodiment of the present invention, the polyhydroxy catalyst is selected from the group consisting of pholoroglucinol, galactose or dextrose.

In a further embodiment of the present invention, the ratio of artemisinin and the polyhydroxy catalyst is in the range of 1:2 to 1:5 w/w.

In one more embodiment of the present invention, the reducing agent is selected from the group consisting of sodium borohydride, lithium aluminium hydride ($LiAlH_4$), lithium tritert-butoxy aluminium gydride ($Li[OC(CH_3)_3]_3 AlH$), lithium trimethoxy aluminium hydride ($Li(OCH_3)_3 AlH$), sodium trimethoxy borohydride ($Na(OCH_3)_3 BH$), sodium bis-2-methoxy, ethoxy aluminium hydride or a mixture of lithium or sodium in alcohol or liquid ammonia.

In one another embodiment of the present invention, the reducing agent is preferably sodium borohydride.

In an embodiment of the present invention, the ratio of artemisinin and sodium borohydride is in the rage of 1:0.5 to 1:0.7 w/w.

In another embodiment of the present invention, the acid catalyst is a solid or a liquid.

In yet another embodiment of the present invention, the liquid acid catalyst is a silylated compound.

In still another embodiment of the present invention, the silylated compound is chlorotrimethysilane.

In one more embodiment of the present invention, the w/v ratio of artemisinin and chlorotrimethysilane is in the range of 1:3 to 1:4.

In one another embodiment of the present invention, the solid acid catalyst is an aromatic sulphonic acid.

In a further embodiment of the present invention, the aromatic sulphonic acid is p-toluene sulphonic acid.

In an embodiment of the present invention, the w/v ratio of artemisinin and p-toluene sulphonic acid is in the range of 1:3 to 1:4.

In another embodiment of the present invention, the acid catalyst is added to the reaction mixture at a temperature in the range of from 10° to 23° C.

In yet another embodiment of the present invention, the extraction of crude arteether from aqueous reaction mixture is carried out with a mixture of 1% ethyl acetate and n-hexane to avoid extraction of unwanted polar impurities.

In still another embodiment of the present invention, the extraction of arteether using the mixture of 1% ethyl acetate and n-hexane may be performed more than once for complete extraction.

In one more embodiment of the present invention, the column us eluted using a gradient mixture of hexane-ethyl acetate having the ratio in the range of 92:8 to 99.5:0.5.

In one another embodiment of the present invention, 80–86% w/w arteether is obtained after purification by silica gel chromatography.

In a further embodiment of the present invention, the arteether obtained is a mixture of alpha and beta arteether in the w/w ratio range of 20:80 to 30:70 w/w.

In an embodiment of the present invention, the conversion of artemisinin into pure arteether takes about 6–8 hours which is significantly less time consuming method.

In another embodiment of the present invention, the yield of the final product i.e. pure alpha, beta arteether by 3–10% w/w as compared to previously reported methods.

To describe in detail, in the process of invention, artemisinin and polyhydroxy catalyst were taken in the ratio of 1:2 to 1:5 w/w and dissolved in ethanol at room temperature and stirred for 5 minutes. Now sodium borohydride is added slowly at the room temperature (20 to 23° C.) and the reaction mixture is stirred for about 0.5 to 1.5 hours.

After completion of the reduction of artemisinin, without workup or the isolation of the dihydroartemisinin, a solid acid catalyst, resin or a liquid acid catalyst, chlorotrimethysilane or trifluroacetic acid is added at 10–20° C. and the reaction mixture is further stirred for about 1 to 2 hours at room temperature.

After completion of the acylation reaction, cooled water is added to the reaction mixture. The solid catalyst is filtered and the filtrate or the aqueous reaction mixture extracted with 1% ethyl acetate in n-hexane. During extraction of the crude arteethers with 1% ethyl-acetate in hexane, the polyhydroxy compound remains in the aqueous phase and is discarded since it is insoluble in hexane-ethyl acetate mixture but soluble in aqueous phase. The combined ethyl acetate-hexane extract is washed with 0.5% sodium bicarbonate solution followed by water.

The extract is dried over anhydrous sodium sulphate and removal of the solvent furnishes impure artemether. Silica gel column chromatography (1:5 to 10 ratio) with 0.5 to 8% ethyl acetate in n-hexane furnishes a mixture of alpha and beta artemether in 80–86% w/w yield.

DESCRIPTION OF THE ACCOMPANYING DRAWINGS

FIG. 1 is a schematic representation of the conversion of artemisinin into arteether.

The following examples are given by way of illustration of the present invention and should not be construed to limit the scope of the present invention.

EXAMPLE 1

Artemisinin (1 g.) and polyhydroxy catalyst, dextrose (5 g.) were stirred in ethanol (20 ml) at room temperature for 5 minutes. Now sodium borohydride (600 mg) was added slowly for 10 minutes and the reaction mixture was stirred for about 1 hour at room temperature (20–23° C.). The reaction was monitored by TLC to check completion of the reduction step. Acid catalyst chlorotrimethysilane (3.5 ml) was added slowly at 10–23° C. and the reaction mixture was further stirred at room temperature for about 1 hour. Cooled water (about 150 ml) was added to the reaction mixture the aqueous reaction mixture was extracted with 1% ethyl acetate in n-hexane (3'50 ml).

The combined ethyl acetate-hexane extract was washed with 0.5% sodium bicarbonate (100 ml) followed by water (50 ml). The n-hexane extract was dried over anhydrous sodium sulphate and evaporation of the solvent yielded 1.038 g. of crude arteether along with some impurities. The impure artemether purified over silica gel (10 g.) with 0.5 to 8% ethyl acetate in hexane furnished a mixture of alpha and beta arteether 0.86 g. (86% w/w). Small portion of arteether was separated by preparative TLC into alpha and beta isomers and characterized by Co-TLC and spectral analysis.

EXAMPLE 2

Artemisinin (1 g.) and polyhydroxy catalyst, dextrose (4 g.) were stirred in ethanol (15 ml). Sodium borohydride (500 mg.) was added slowly for 10 minutes and the reaction mixture was stirred for 30 minutes at room temperature (20–23° C.). After completion of the reduction step, chlorotrimethysilane (3.5 ml) was added and the reaction mixture was further stirred for 1.5 hours at room temperature. After usual work up and purification through column chromatography (1:5 ratio) a mixture of alpha and beta arteether (0.805 g., 80.5% w/w) were obtained.

EXAMPLE 3

Artemisinin (1 g.) and polyhydroxy catalyst, dextrose (2 g.) were stirred in ethanol (25 ml). Sodium borohydride (700 mg.) was added slowly for 10 minutes and the reaction mixture was stirred for 1.5 hours at room temperature (20–23° C.). After completion of the reduction step, chlorotrimethysilane (4 ml) was added and the reaction mixture was further stirred for 2 hours at room temperature (20–23° C.) to give 0.95 g. of crude arteether. After usual work up and purification through column chromatography 0.95 g. of crude arteether yielded 0.825 g. of a mixture of alpha and beta arteether (82.5% w/w).

EXAMPLE 4

Artemisinin (100 g.) and polyhydroxy catalyst, dextrose (500 mg.) were stirred in ethanol (10 ml) for 5 minutes. Sodium borohydride (65 mg.) was added slowly to the reaction mixture and the same was stirred for 1.25 hours at room temperature (20–23° C.). After completion of the reduction step, p-toluene sulphonic acid (300 mg.) was added and the reaction mixture was completed in 4 hours at room temperature. After usual work up and purification by preparative TLC, the impure reaction product yielded 53% w/w a mixture of alpha and beta arteether.

EXAMPLE 5

Artemisinin (100 g.) and polyhydroxy catalyst, galactose (300 mg.) were stirred in ethanol (5 ml) for 5 minutes. Sodium borohydride (60 mg.) was added slowly to the reaction mixture and the same was stirred for 1.5 hours at room temperature (20–23° C.). After completion of the reduction step, liquid acid catalyst chlorotrimethysilane (0.35 ml) was added and the reaction mixture was further stirred for 2 hours to complete the reaction. After usual work up and purification by preparative TLC, the impure reaction product afforded 62% w/w of a mixture of alpha and beta arteether.

EXAMPLE 6

Artemisinin (100 g.) and polyhydroxy catalyst, phloroglucinol (400 mg.) were stirred in ethanol. Sodium borohydride (65 mg.) was added slowly to the reaction mixture and the same was stirred for 2 hours at room temperature (20–23° C.). After completion of the reduction step, chlorotrimethysilane (0.8 ml) was added and the reaction mixture was further stirred for 2 hours at room temperature to complete the reaction. Work up and purification of the crude product by preparative TLC yielded 74% w/w a mixture of alpha and beta arteether.

What is claimed is:

1. A single pot process for the preparation of arteether from artemisinin comprising the steps of:
   (a) dissolving artemisinin and a polyhydroxy catalyst in ethanol at room temperature to obtain a solution,
   (b) adding a reducing agent to step (a) solution, stirring the reaction mixture at a temperature ranging between 20 to 30° C. for about 0.5 to 2 hours to reduce artemisinin into dihydroartemisinin,
   (c) adding an acid catalyst to the reaction mixture of step (b) with cooling,
   (d) stirring the reaction mixture of step (c) for about 1 to 2 hours at room temperature,
   (e) adding cold water to the reaction mixture of step (d), extracting with a mixture of ethyl acetate and n-hexane, separating the organic layer, (f) washing the organic layer of step (e) with 0.5% aqueous sodium bicarbonate solution followed by water, (g) drying the washed organic layer of step (f) over anhydrous sodium sulphate, filtering, evaporating the organic layer to obtain a residue, and (h) purifying the residue of step (g) by silica gel column chromatography to obtain arteether.

2. A process as claimed in claim 1, wherein the two reactions, namely reduction of artemisinin to dihydroartemisinin and alkylation of dihydroartemisinin into arteether are carried out in a single pot thereby avoiding the process of isolation of the intermediate dihydroartemisinin.

3. A process as claimed in claim 1, wherein the time required for conversion of artemisinin into arteether is about 4 hours.

4. A process as claimed in claim 1, wherein ethanol used acts as a solvent and an alkylating agent.

5. A process as claimed in claim 1, wherein the polyhydroxy catalyst is selected from the group consisting of pholoroglucinol, galactose or dextrose.

6. A process as claimed in claim 1, wherein the ratio of artemisinin and the polyhydroxy catalyst is in the range of 1:2 to 1:5 w/w.

7. A process as claimed in claim 1, wherein the reducing agent is selected from the group consisting of sodium borohydride, lithium aluminium hydride ($LiAlH_4$), lithium tritertbutoxy aluminium gydride ($Li[OC(CH_3)_3]_3$ AlH), lithium trimethoxy aluminium hydride ($Li(OCH_3)_3$ AlH), sodium trimethoxy borohydride ($Na(OCH_3)_3$ BH), sodium bis-2-methoxy, ethoxy aluminium hydride or a mixture of lithium or sodium in alcohol or liquid ammonia.

8. A process as claimed in claim 7, wherein the reducing agent is sodium borohydride.

9. A process as claimed in claim 1, wherein the ratio of artemisinin and sodium borohydride is in the rage of 1:0.5 to 1:0.7 w/w.

10. A process as claimed in claim 1, wherein the acid catalyst is a liquid or a solid.

11. A process as claimed in claim 10, wherein the liquid acid catalyst is a silylated compound.

12. A process as claimed in claim 11, wherein the silylated compound is chlorotrimethysilane.

13. A process as claimed in claim 12, wherein the w/v ratio of artemisinin and chlorotrimethysilane is in the range of 1:3 to 1:4.

14. A process as claimed in claim 10, wherein the solid acid catalyst is an aromatic sulphonic acid.

15. A process as claimed in claim 14, wherein the aromatic sulphonic acid is p-toluene sulphonic acid.

16. A process as claimed in claim 15, wherein the w/w ratio of artemisinin and p-toluene sulphonic acid is in the range of 1:3 to 1:4.

17. A process as claimed in claim 1, wherein the acid catalyst is added to the reaction mixture at a temperature in the range of from 10 to 23° C.

18. A process as claimed in claim 1, wherein the extraction of crude arteether from aqueous reaction mixture is carried out with a mixture of 1% ethyl acetate and n-hexane to avoid extraction of unwanted polar impurities.

19. A process as claimed in claim 18, wherein the extraction of arteether using the mixture of 1% ethyl acetate and n-hexane may be performed more than once for complete extraction.

20. A process as claimed in claim 1, wherein column is eluted using a gradient mixture of hexane-ethyl acetate having the ratio in the range of 92:8 to 99.5:0.5.

21. A process as claimed in claim 1, wherein 80–86% w/w arteether is obtained after purification by silica gel chromatography.

22. A process as claimed in claim 1, wherein the arteether obtained is a mixture of alpha and beta arteether in the w/w ratio range of 20:80 to 30:70.

* * * * *